US011972867B2

(12) United States Patent
Sanduleanu et al.

(10) Patent No.: US 11,972,867 B2
(45) Date of Patent: Apr. 30, 2024

(54) METHOD OF TRAINING A MACHINE LEARNING DATA PROCESSING MODEL, METHOD OF DETERMINING A HYPOXIA STATUS OF A NEOPLASM IN A HUMAN OR ANIMAL BODY, AND SYSTEM THEREFORE

(71) Applicant: Universiteit Maastricht

(72) Inventors: Sebastian Sanduleanu, Brunssum (NL); Philippe Lambin, Bousval-Genappe (BE)

(73) Assignee: Universiteit Maastricht, Maastricht (NL)

( * ) Notice: Subject to any disclaimer, the term of this patent is extended or adjusted under 35 U.S.C. 154(b) by 805 days.

(21) Appl. No.: 17/123,816

(22) Filed: Dec. 16, 2020

(65) Prior Publication Data
US 2021/0217525 A1 Jul. 15, 2021

(30) Foreign Application Priority Data

Dec. 17, 2019 (NL) ...................................... 2024482

(51) Int. Cl.
*G16H 50/20* (2018.01)
*G06N 5/01* (2023.01)
(Continued)

(52) U.S. Cl.
CPC ............... *G16H 50/20* (2018.01); *G06N 5/01* (2023.01); *G06N 20/20* (2019.01); *G06T 7/0012* (2013.01);
(Continued)

(58) Field of Classification Search
CPC ........ G16H 50/20; G16H 20/40; G16H 30/20; G16H 30/40; G06N 5/01; G06N 20/20;
(Continued)

(56) References Cited

U.S. PATENT DOCUMENTS

2017/0109472 A1    4/2017   Dominick et al.

FOREIGN PATENT DOCUMENTS

EP    2695579 A1    2/2014

OTHER PUBLICATIONS

Even et al., Predicting tumor hypoxia in non-small cell lung cancer by combining CT, FDG PET and dynamic contrast-enhanced CT, 2017, Acta Oncologica, 2017, vol. 56, No. 11, 1591-1596 (Year: 2017).*

(Continued)

*Primary Examiner* — Said M Elnoubi
(74) *Attorney, Agent, or Firm* — Banner & Witcoff, Ltd.

(57) ABSTRACT

The present document describes a training method of a machine learning data processing model for determining a hypoxia status of a neoplasm, in particular a random forest model. The method comprises obtaining, for a plurality of neoplasms, at least one data sample comprising 3D imaging data. A hypoxic volume fraction is determined for each data sample, as well as a set of image features associated with the neoplasm. The method further iterates a sequence of training steps and each iteration includes: selecting a subset of image features and eliminating, for each data sample, the subset of image features to yield a reduced set of image features. The iteration also includes generating decision trees, providing a momentary random forest model based thereon, and submitting a test set of image features to the momentary random forest model to yield a performance value. The iterations are continued until all image features have been selected for a subset at least once, and then a plurality of preferred image features are selected for providing a radiomics feature signature. The trained random forest data processing model based on decision trees associated with the preferred image features of the radiomics feature signature.

20 Claims, 9 Drawing Sheets

(51) Int. Cl.
  *G06N 20/20* (2019.01)
  *G06T 7/00* (2017.01)
  *G16H 20/40* (2018.01)
  *G16H 30/20* (2018.01)

(52) U.S. Cl.
  CPC ............. *G16H 20/40* (2018.01); *G16H 30/20* (2018.01); *G06T 2207/20081* (2013.01); *G06T 2207/30004* (2013.01)

(58) Field of Classification Search
  CPC ......... G06T 7/0012; G06T 2207/20081; G06T 2207/30004
  See application file for complete search history.

(56) References Cited

OTHER PUBLICATIONS

Sep. 9, 2020—Dutch Search Report—NL 2024482.
Davatzikos Christos Ed—Johansen-Berg Heidi et al, NeuroImage, Elsevier, deel 197, Oct. 6, 2018 (Oct. 6, 2018), bladzijden 652-656.
Fanny Orlhac et al, Radiology, deel 291, nr. 1, Apr. 1, 2019 (Apr. 1, 2019), bladzijden 53-59.
Jean-Philippe Fortin et al, NeuroImage, deel 167, Feb. 1, 2018 (Feb. 1, 2018), bladzijden 104-120.
Blumberg Stefano B et al, European Conference on Computer Vision, ECCV , pp. 411-419.
Ibrahim Abdalla et al., Seminars in Nuclear Medicine, deel 49 nr. 5 (2019)438-449.
Sanduleau D et al., Radiotherapy and Oncology, deel 133 nr. suppl. 1 (2019) S376-S377.
Michele Avanzo et al., Medical Physics, deel 10 nr. 5 (2020).
Philippe Lambin et al., Nature Reviewus Clinical Oncology, deel 14 nr. 12(2017)749-762.
Mireia Crispin-Ortuzar et al., Radiotherapy and Oncology, deel 127 nr. 1 (2018)36-42.
Aniek J. G. Even et al., Acta Oncologica, deel 56, nr. 11(2017)1591-1596).
Marta Bogowicz et al., Scientific report, deel 10 nr. 1 (2020) 4542.
Sebastian Sanduleanu et al., Cancers, deel 12 nr. 5 (2020)1322.
Eric Dinges et al. "Bone Marrow Sparing in Intensity Modulated Proton Therapy for Cervical Cancer: Efficacy and Robustness under Range and Setup Uncertainties" Jun. 1, 2016.
Penny Fang, MD et al. "Lymphocyte-Sparing Effect of Proton Therapy in Patients with Esophageal Cancer Treated with Definitive Chemoradiation" Mar. 21, 2018.

* cited by examiner

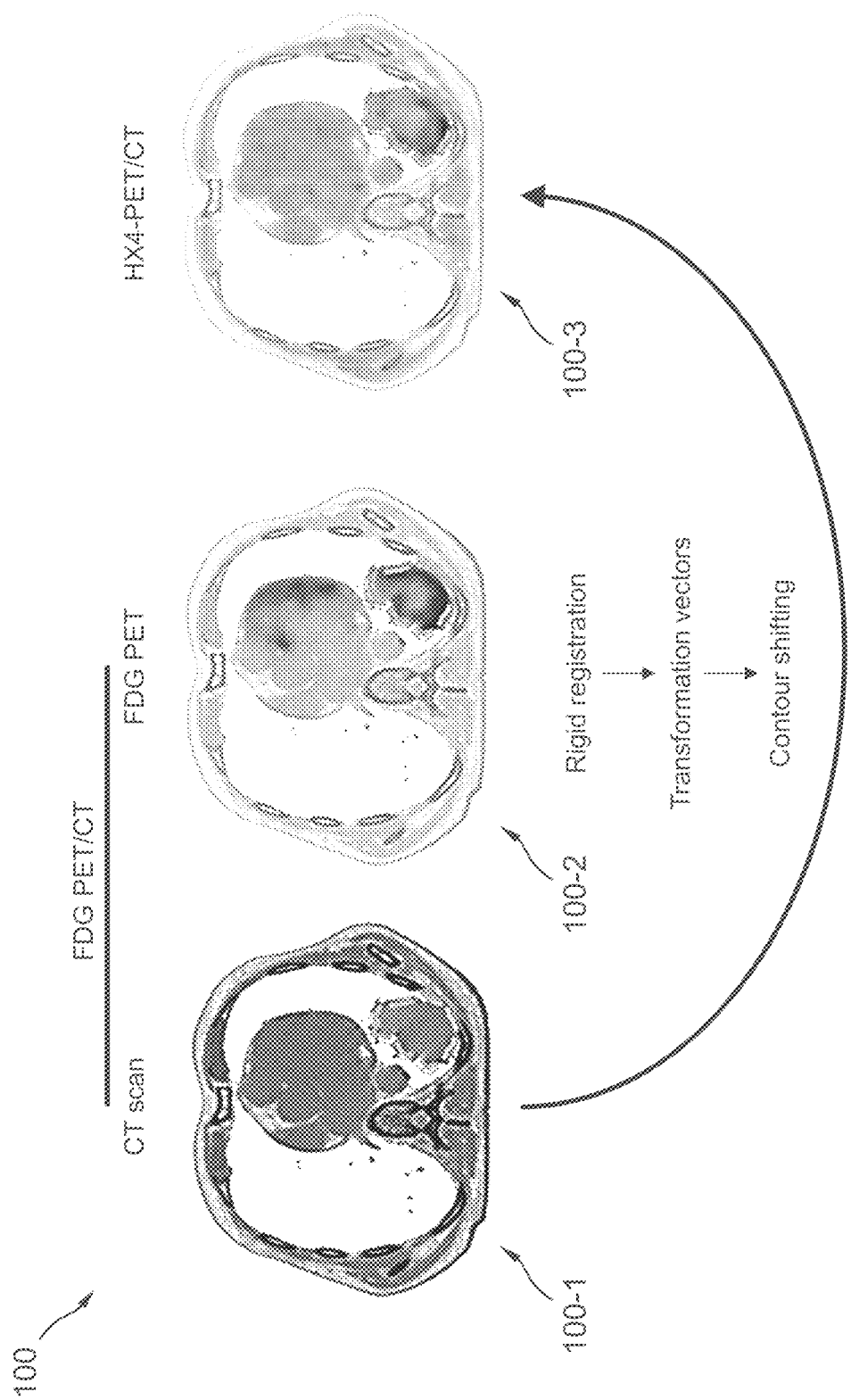

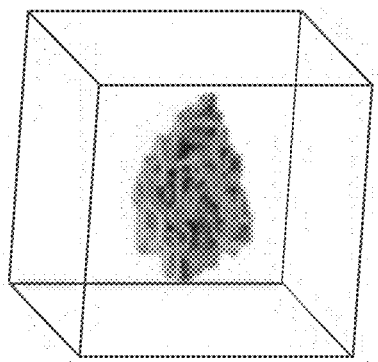
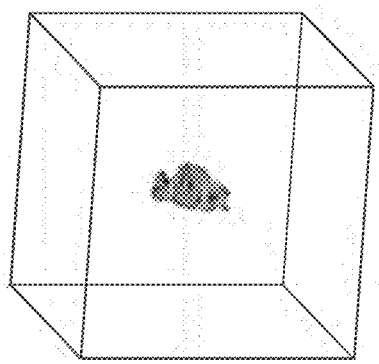
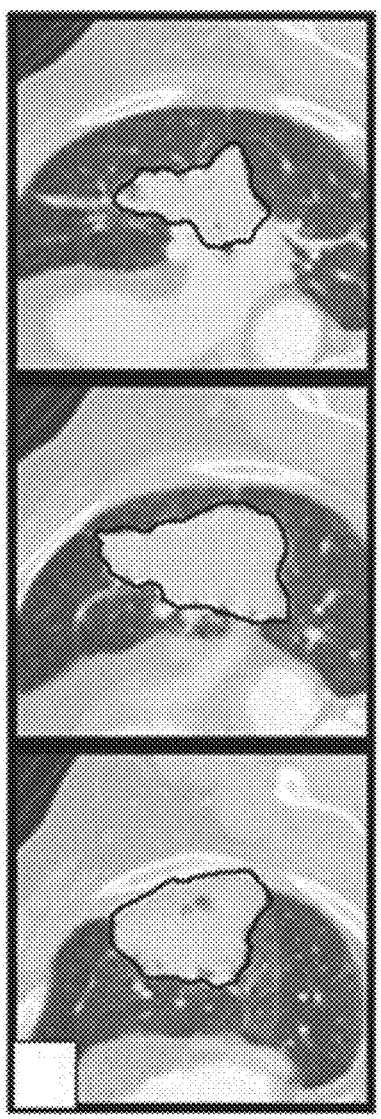
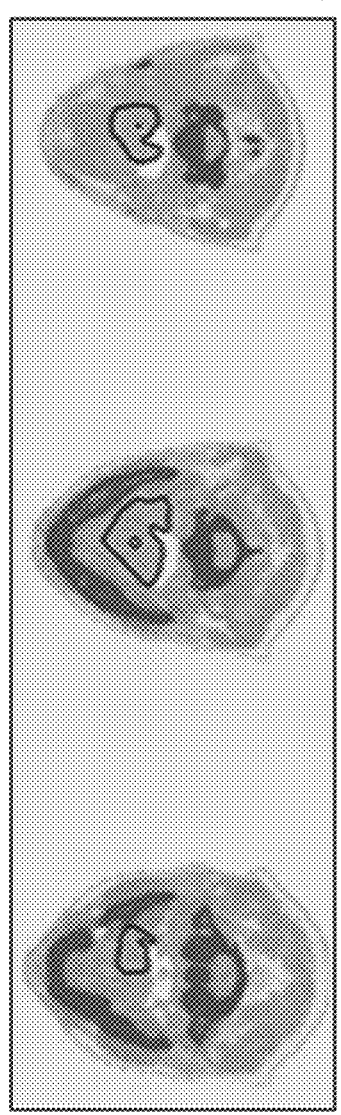
Fig. 2B
Fig. 2C

METHOD OF TRAINING A MACHINE LEARNING DATA PROCESSING MODEL, METHOD OF DETERMINING A HYPOXIA STATUS OF A NEOPLASM IN A HUMAN OR ANIMAL BODY, AND SYSTEM THEREFORE

CROSS-REFERENCE TO RELATED APPLICATIONS

This application claims priority to Dutch patent application NL 2024482, filed Dec. 17, 2019, which is hereby incorporated by reference in its entirety.

FIELD OF THE INVENTION

The invention relates to methods and systems for determining a hypoxia status of a neoplasm.

DESCRIPTION OF RELATED ART

A tumor is considered clinically radioresistant when it insufficiently responds to treatment by radiotherapy. One of the major known causes of radio resistance and resistance to systemic therapy (e.g. chemotherapy, hormonal therapy as well as immunotherapy), is tumor hypoxia. Cells that are hypoxic at the time of irradiation suffer less damage from a given radiation dose than do oxygenated cells. Thus, a greater number of hypoxic cells within a tumor makes it more radioresistant and resistant to systemic therapy.

For the above reasons, in order to estimate the expected chance of successfully treating a patient with radiotherapy, systemic therapy or other treatment, having insight in the hypoxia status of the neoplasm is advantageous. However, it is not straightforward to determine the hypoxia status from routine clinical images of the neoplasm obtained. Each scanner has its own settings that may differ from that of others, and there are images obtained using various different imaging techniques.

Another issue is that in order to determine hypoxia presently, use has to be made of hypoxia PET-imaging tracers such as [$^{18}$F]-HX$_4$ or other similar markers. These substances are very expensive and have highly time consuming acquisition protocols, hence for each patient it has to be decided whether or not the step of determining tumor hypoxia using such markers is beneficial.

SUMMARY OF THE INVENTION

It is an object of the present invention to overcome the above disadvantages and to provide a method of determining a hypoxia status of a neoplasm without necessarily requiring hypoxia PET-tracers and invasive markers.

To this end, there is provided herewith a method of training a machine learning data processing model for determining a hypoxia status of a neoplasm in a human or animal body, wherein the machine learning data processing model is a random forest data processing model, the method comprising: obtaining, for each of a plurality of neoplasms, at least one data sample comprising three dimensional imaging data of said respective neoplasm; determining, for each data sample, a hypoxic fraction of the neoplasm by identifying a volume fraction of a total volume of the neoplasm which is indicative of hypoxia, and associating the determined hypoxic fraction with the respective data sample; determining, for each data sample, a set of image features comprising a plurality of image features associated with the neoplasm, and wherein each image feature of the set of image features is characterized by an image feature parameter value that is derived from the image data; iterating a sequence of training steps, wherein the sequence in each iteration includes: selecting, for the respective iteration, a subset of image features from the set of image features, wherein at least a part of the selected image features for the subset has not been selected during a preceding iteration; eliminating, for each data sample, the subset of image features from the set of image features to yield a reduced set of image features; generating, based on the reduced sets of image features for the plurality of data samples and the hypoxic fractions associated with the data samples, a plurality of decision trees and providing a momentary random forest model based on the decision trees; submitting, for at least one test data sample, a test set of image features to the momentary random forest model to determine the hypoxia status for the at least one test data sample, and compare the determined hypoxia status with the hypoxia fraction associated with the test data sample to yield a performance value; continue the step of iterating until each of the image features has been selected for a subset at least once; selecting, by evaluating the performance values, a plurality of preferred image features from the set of image features for providing a radiomics feature signature including the preferred image features; and providing the trained random forest data processing model based on decision trees associated with the preferred image features of the radiomics feature signature.

The invention is based on the insight that, by training a random forest model as described above, hypoxia status of a neoplasm may easily be determined on the basis of image features, and even radiomics signatures can be developed that allow evaluating the hypoxia status of a neoplasm in absence of the trained random forest data processing model.

As non-limiting examples, the volume fraction of the total volume of the neoplasm which is indicative of hypoxia may be determined on the hypoxia positron emission tomography (PET) imaging data (e.g. HX4-PET). The set of image features may be determined both on computed tomography (CT) and where available fluorodeoxyglucose positron emission tomography (FDG-PET) associated with the hypoxia PET scan. However, other imaging methods that allow the hypoxic volume fraction of the total volume of the neoplasm to be determined may likewise be applied to obtain this data. Likewise, the set of image features may be determined based on other imaging methods, and the invention is not limited to the abovementioned well working embodiments.

In some embodiments, the momentary random forest models and the trained random forest data processing model are at least one of: classifier models, wherein the hypoxia status provides a Boolean indication on whether or not a data sample is indicative of a hypoxic neoplasm; or regression models, wherein the hypoxia status provides an expectation value of a hypoxic fraction of the neoplasm associated with the data sample. A Boolean indicator could be a binary indicator, such as a flag to be set or a binary number to be provided as output. For example, the number may be set to "1", "true" or "y" in case a data sample is indicative of a hypoxic neoplasm, and "0", "false" or "n" in case a data sample is not indicative of a hypoxic neoplasm. As may be appreciated, without loosing any functionality, this may be inverted if desired, i.e. "0" for hypoxic data samples and "1" for non-hypoxic data samples. Also, other Boolean operators or binary values may be applied.

In some embodiments, the imaging data is obtained after administration of a hypoxiaPET tracer, and wherein, for determining the hypoxia fraction, the volume fraction of the total volume of the neoplasm is identified wherein a standard uptake value of the hypoxia PET tracer is above a threshold value. The threshold of the standard uptake value may be dependent on a number of factors, and may thus be determined dependent on the circumstances or by trial and error after a number of different runs of the training method and after evaluation of the results. The invention is not limited to a specific threshold value, although below some embodiments will be presented for which good results have been achieved.

For example, in some of the above embodiments, determining the hypoxia fraction comprises the steps of: determining an average standard uptake value of the hypoxia staining marker in at least a region of the neoplasm; determining, for each voxel of a plurality of voxels within the region, a standard uptake value of the respective voxel; flagging the respective voxel as a hypoxic voxel if the standard uptake value of the voxel is greater than or equal to 1.4 times the average standard uptake value of the region; and flagging the respective voxel as a non-hypoxic voxel if the standard uptake value of the voxel is smaller than 1.4 times the average standard uptake value of the region; counting a total number of voxels and a total number of hypoxic voxels, and calculating the hypoxic fraction by dividing the total number of hypoxic voxels by the total number of voxels. As stated above, although good results have been achieved with the above embodiment, the skilled person may decide to deviate from the number of 1.4 where desired, e.g. use values within a range of 1 to 2, preferably within a range of 1.2 to 1.6, without departing from the claimed invention. Furthermore, determining the average standard uptake value in at least a region of the neoplasm refers to obtaining a reference value. As a reference value, a background hypoxia level of muscle or aorta tissue may be applied. However, the skilled person will appreciate that useable values may likewise be obtained from other tissue without departing from the invention.

In some embodiments, after obtaining the data samples, one or more of the data samples are selected as test data samples forming a test fraction and wherein the other data samples of the plurality of data samples provide a training fraction, wherein at least a part of the selected test data samples has not been selected as test data samples during a preceding pass of the method; wherein the step of generating decision trees for providing the momentary random forest model is performed based on the training fraction and wherein submitting the test set of image features to the momentary random forest model is performed based on the test fraction; wherein the method is repeated in a plurality of passes.

In some embodiments, the method is repeated until all data samples of the plurality of data samples have been selected as test data samples at least once.

In some embodiments, the step of generating the plurality of decision trees comprises generating each decision tree as a sequence of decisions wherein each decision is based on one or more image features of the reduced set, and wherein for selecting the preferred image features the image features are ranked based on the performance values and one or more image features having lowest performance values are discarded.

Where the method is performed in passes, in some of these embodiments, wherein for selecting the preferred image features, during each pass one or more image features having lowest performance values are discarded, such as to yield the preferred image features at the end of the last pass of the method.

In some embodiments, after having determined the hypoxic fractions of each of the plurality of data samples, a total number of data samples having an associated hypoxic fraction indicative of a hypoxic neoplasm is compared with a total number of data samples having an associated hypoxic fraction indicative of a non-hypoxic neoplasm, and wherein one or more data samples are repeated or discarded if a difference between the total number of hypoxic neoplasms and the total number of non-hypoxic neoplasm exceeds a threshold, such as to balance the data samples used for training the random forest data processing model. In some embodiments, the threshold is a difference exceeding 20%, preferably a difference exceeding 10%, more preferably 5%.

In some embodiments, a neoplasm associated with a data sample is flagged as a hypoxic neoplasm if the hypoxic fraction is above at least one of: 10%, 20%, or 30%, preferably if the hypoxic fraction is above 20%.

In some embodiments, the data samples have been obtained using a plurality of different imaging systems, and wherein the method further comprises a step of harmonizing the image features such that the characteristic image feature parameter values are quantitatively comparable between said different imaging systems.

In some embodiments, the step of obtaining data samples is performed by selecting data samples of a plurality of neoplasms of a specific phenotype.

In some embodiments, the neoplasms of the specific phenotype include at least one of a group comprising: head and neck type tumors, lung tumors.

In accordance with a second aspect, there is provided a method of determining a hypoxia status of a neoplasm in a human or animal body, wherein the method comprises: obtaining using an imaging system three dimensional imaging data of said the neoplasm for providing a data sample; determining a plurality of image features from the data sample wherein each image feature is characterized by an image feature parameter value that is derived from the image data; submitting the plurality of image features to a trained random forest data processing method; wherein the trained random forest data processing model is trained using a method according to the first aspect, and wherein the plurality of image features at least include the preferred image features of the radiomics feature signature.

In accordance with a second aspect, there is provided a system for determining a hypoxia status of a neoplasm in a human or animal body, wherein the system comprises a memory, a controller and input means, wherein the input means are configured for receiving a data sample comprising three dimensional imaging data of a neoplasm, wherein the memory has stored therein data descriptive of a trained random forest data processing model that has been trained using a method according to the first aspect, wherein the controller is configured for cooperating with the memory such as to perform a method according to the second aspect.

BRIEF DESCRIPTION OF THE DRAWINGS

The invention will further be elucidated by description of some specific embodiments thereof, making reference to the attached drawings. The detailed description provides examples of possible implementations of the invention, but is not to be regarded as describing the only embodiments falling under the scope. The scope of the invention is defined in the claims, and the description is to be regarded as illustrative without being restrictive on the invention. In the drawings:

FIG. 1 illustrates the calculation of hypoxia fractions using Reggui software v.1357, for use with the present invention;

FIGS. 2A, 2B, and 2C provide various 3D and 2D sliced images of hypoxic tumours;

DETAILED DESCRIPTION

Figure 2A:
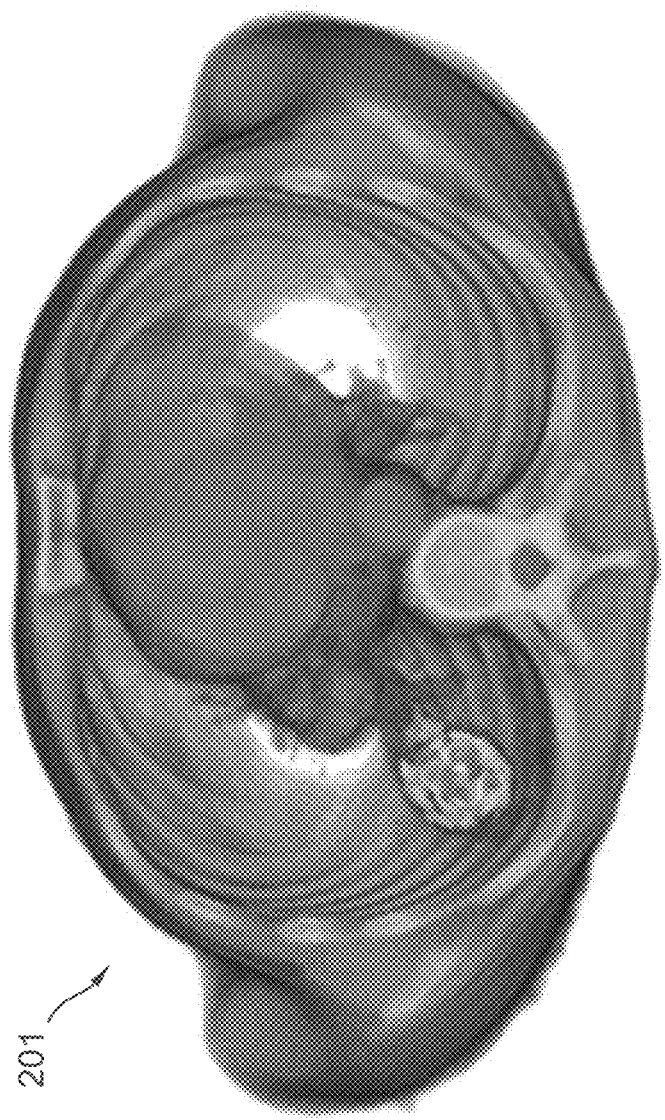

Background: Tumor hypoxia increases resistance to radiotherapy and systemic therapy. Our aim was to develop and validate an agnostic and site-specific CT and FDG-PET-based radiomics hypoxia classification signature.

Material and Methods: A total of 808 patients from 8 registered prospective clinical trials were included in the generation and validation of the CT and FDG-PET hypoxia classification signature, from which 221 patients with ground-truth hypoxia-PET: 131 patients with [$^{18}$F]-HX4 PET, 14 patients with up to three [$^{18}$F]-FAZA imaging timepoints (n=36) and 76 patients with [$^{18}$F]-FMISO-PET. The primary gross tumor volumes (GTV) were manually defined on CT. In order to dichotomize between hypoxic/well-oxygenated tumors a threshold of 20% was used for the [$^{18}$F]-HX4-derived hypoxic fractions (HF, defined as the ratio between the high uptake hypoxic regions with tumor-to-background ratio>1.4 to total GTV), aside from a lower range of 10%, upper range of 30% and treating the HF as a continuous outcome variable. A random forest (RF)-based machine-learning classifier/regressor was trained to classify patients as hypoxia-positive/negative based on radiomic features.

Results: An agnostic CT model to classify hypoxia status (HF cutoff 20%) reached AUC's of respectively 0.79±0.16, 0.76±0.18 and 0.72±0.14 respectively in three external validation datasets by combining 5 CT-derived radiomic features. An agnostic FDG-PET model reached an AUC of 0.74±0.23 in external validation by combining 10 features (HF cutoff 20%). The lung-specific model reached an AUC of 0.80±0.15 in external validation with 4 CT features, while the H&N-specific model reached an AUC of 0.86±0.20 in external validation with 6 CT features. A significant survival split (P=0.037) was found between CT-classified hypoxia strata in an external H&N cohort (n=517), while 117 significant but low hypoxia gene-CT signature feature associations were found in an external lung cohort (n=80).

Conclusion: Our hypoxia signatures have the potential to enrich interventional hypoxia-targeting trials by identifying patients with tumors likely to be hypoxic.

Highlights

The validated CT/FDG-PET hypoxia signature showed favorable discriminatory ability.

A significant survival split was found between CT-classified hypoxia strata.

There were 117 significant yet low hypoxia gene-CT signature feature associations.

By identifying hypoxic patients we can potentially "enrich" HAP trials.

This study provides new insights into the current limitations of hypoxia-PET imaging.

Introduction

Since the early 1930s, it has been established that solid tumors contain oxygen-deficient (hypoxic) areas. Cells in such areas may cause tumors to become resistant to radiotherapy and chemotherapy, increase tumor aggressiveness, angiogenesis, and metastatic spread, resulting in a poor prognosis.

Over the past decades various techniques have been used to determine solid tumor oxygenation status, including hypoxia staining markers (e.g. 2-nitroimidazoles) and noninvasive quantitative PET imaging (most commonly [$^{18}$F]-FMISO, [$^{18}$F]-HX4, [$^{18}$F]-FAZA as well as other 2-nitroimidazoles). In an effort to validate the heterogeneous uptake of [$^{18}$F]-HX4 at the regional tumor level, a preclinical study found that [$^{18}$F]-HX4 derived hypoxic fractions (HF) in tumors are strongly correlated with HF's assessed by the staining marker pimonidazole. Furthermore, a causal inference was observed between the pretreatment tumor oxygenation status (HF's were altered bycarbogen/nicotinamide exposure) measured by [$^{18}$F]-HX4 and the treatment efficacy with a hypoxia activated pro-drug (HAP) TH302 that selectively kills hypoxic cells. Hypoxia PET imaging is difficult to implement in clinical practice since these PET-agents generally tend to generate smaller signal-to-background ratios compared to e.g. [$^{18}$F]-FDG (and consequently lower target-background image contrast), imaging is labor intensive (instruction multiple bed positions and acquisitions at multiple time point), costly (chemical process to produce the radio ligand is slightly more expensive) and lacking of standard calibration procedures and inconvenient for the patient due to the time-consuming acquisition protocols.

Several HAP trials have failed to demonstrate efficacy in pivotal clinical trials (e.g. Tirapazamine, Evofosfamide), putatively due to the lack of patient selection with clearly defined high levels of hypoxia. Another contributing factors might be the complex biology and spatiotemporal heterogeneity of the target (e g difficulties with extravascular transport to target cells, high variability in hypoxic compartments in relatively short periods of time).

Computed Tomography (CT) and $^{18}$F-FDG-PET imaging, by contrast, are both routinely used in clinical practice for cancer diagnosis and treatment planning. Radiomics is a mathematical procedure to determine statistical properties of an image using data-characterisation algorithms in order to derive imaging biomarkers.

This current study expands on previous initiatives in hypothesizing that radiomic biomarkers from CT and FDG-PET imaging can be used to identify tumour with considerable hypoxic regions, as established using HX4-PET, FMISO-PET and FAZA-PET. It is thus essential to obtain a good understanding of the functional relationship of these features and the underlying intra-tumoral hypoxia status. With these characteristics we believe that we can "enrich" e.g. window-of opportunity trial populations using CT- and FDG-PET-based radiomics to identify hypoxic patients.

The aim of this study was to develop an agnostic (multiple tumor sites) and site specific HX4 derived CT an FDG-PET based radiomics hypoxia signature, validate this on an external datasets and assess the prognostic value of the signature and their association with previously validated hypoxia-response genes. We hypothesize that a combination of CT and FDG-PET-derived features could lead to a model with a higher performance compared to either modality alone.

Materials and Methods

Patient Selection

Patients from six academic medical centers and eight registered clinical trials were included (Supplementary appendix A and B), consisting of six [$^{18}$F]-HX4 datasets, one [$^{18}$F]-FAZA dataset, one [$^{18}$F]-FMISO and one based on the exogenous immunohistochemical marker pimonidazole (a 2-nitroimidazole derivate). IRB approval was obtained for this retrospective analysis and informed consent was given from all patients in the individual trials.

Image Acquisition

All patients underwent pretreatment diagnostic CT/planning [$^{18}$F]-FDG PET/CT. Pretreatment [$^{18}$F]-HX4 PET static images were acquired 2 and/or 4 hours post injection (h.p.i.). When available, only the 4 h.p.i. images were used, since this time point is related to a plateau phase in tracer uptake that has been associated with optimal imaging properties. In the Boston and UCL dataset only 2 h p.i. images were available, and according to previous literature a tumor-to-background ratio (TBR) threshold of 1.2 was used instead of 1.4. Details regarding the acquisition parameters, protocol, and scanner types are presented in Supplementary appendix B, including an analysis of the $SUV_{mean}$ in the background ROI as function of PET-tracer acquisition times for 10 random HX4-PET, FAZA-PET and FMISO-PET patients with head and neck squamous cell carcinoma.

Image Segmentation, Analysis and Ground Truth Hypoxia

Primary gross tumor volumes (GTV) were manually defined on CT by experienced radiation oncologists/radiologists. [$^{18}$F]-FDG PET images were included only if they were performed within a week prior or after [$^{18}$F]-HX4 PET imaging, to mitigate for the temporal changes in tumor hypoxia. For the lung, and H&N cancer cases the clinical delineations defined on the planning [$^{18}$F]-FDG PET/CTs were transferred to the [$^{18}$F]-HX4 CT by means of rigid registration with Mirada software v 1.2.0.59 (Mirada Medical, Oxford, UK). Air and bone were filtered out using windowing presets and the delineations were manually adjusted to reflect small anatomical changes. For the esophageal and pancreatic cancer cases repeated scans of the same patient were rigidly co-registered to match the first scan using the mutual information metric, followed by a rigid registration. The corresponding PET images were subsequently registered using the resultant registration vectors. After registration, the tumor area in the esophagus or pancreas, and the aorta were drawn on the [$^{18}$F]-HX4 CT. Separately acquired diagnostic contrast enhanced CT images were used as reference for better tumor localization.

Cutoffs of 10%, 20% and 30% were used for hypoxic fractions (HF) to dichotomize between well-oxygenized and hypoxic tumors, in accordance with previous studies. For the calculation of HF's, the following steps (See FIG. 1.) were followed in Reggui software v.1357 (OpenReggui, Louvain-la-Neuve, Belgium): i) Contour GTV and aorta/muscle contour on HX4-CT. ii) Resample and register HX4-PET to HX4-CT. iii) Transfer GTV and aorta/muscle contour to HX4-PET. iv) Calculate average $SUV_{aorta}$ and average $SUV_{muscle}$ (dependent on tumour site). v) On HX4-PET flag voxels as hypoxic (1) if SUV uptake per voxel/(mean aorta OR muscle uptake)≥1.4 and non-hypoxic (0) if SUV uptake/(mean aorta OR muscle uptake)<1.4. vi) Calculate a HF as the number of hypoxic voxels/total number of VOI voxels. Additionally patients from a separate validation dataset (ARCON-trial) with fresh frozen biopsies obtained after 20-min i.v. infusion of 500 mg/m$^2$ of hypoxia marker Hypoxyprobe-1 (pimonidazole hydrochloride; NPI, Inc., Belmont, MA) were analyzed for association of the hypoxia radiomics signature with underlying histopathology. For these cases the HF was defined as the tumor area positive for pimonidazole relative to the total tumor area in immunohistochemical analysis.

Image Pre-processing and Radiomic Feature Extraction/Harmonization

International Biomarker Standardization Initiative (IBSI)-compliant radiomic features (https://ibsi.readthedocs.io/) as well as other non-IBSI covered features were extracted from both pretreatment [$^{18}$F]-HX4-CT's as well as diagnostic [$^{18}$F]-FDG PET with our in-house RadiomiX research software (supported by Oncoradiomics, Liège, Belgium) implemented in Matlab 2017a (Mathworks, Natick, Mass). Houndsfield Unit (HU) intensities beyond −1024 and +3071 HU were clipped (assigned the value −1024 and +3071 respectively). An image intensity discretization with a fixed bin width of 25 Houndsfield Units (HU) and a standardized uptake value (SUV) of 0,50 was used for feature extraction in CT and FDG-PET respectively. Voxel size resampling (i.e., image interpolation) was omitted for the agnostic model (See FIG. 3.) in order to capture the full variability of the imaging data.

A total of 1222 CT and 1340 PET features were extracted from each image, consisting of five main groups: 1) fractal features 2) first order statistics, 3) shape and size, 4) texture descriptors including gray level co-occurrence (GLCM), gray level run-length (GLRLM) and gray level size-zone texture matrices (GLSZM), 5) features from groups 1, 3 and 4 after wavelet decomposition. There were no missing feature values. Definitions and detailed feature descriptions are described elsewhere.

Figure 3:
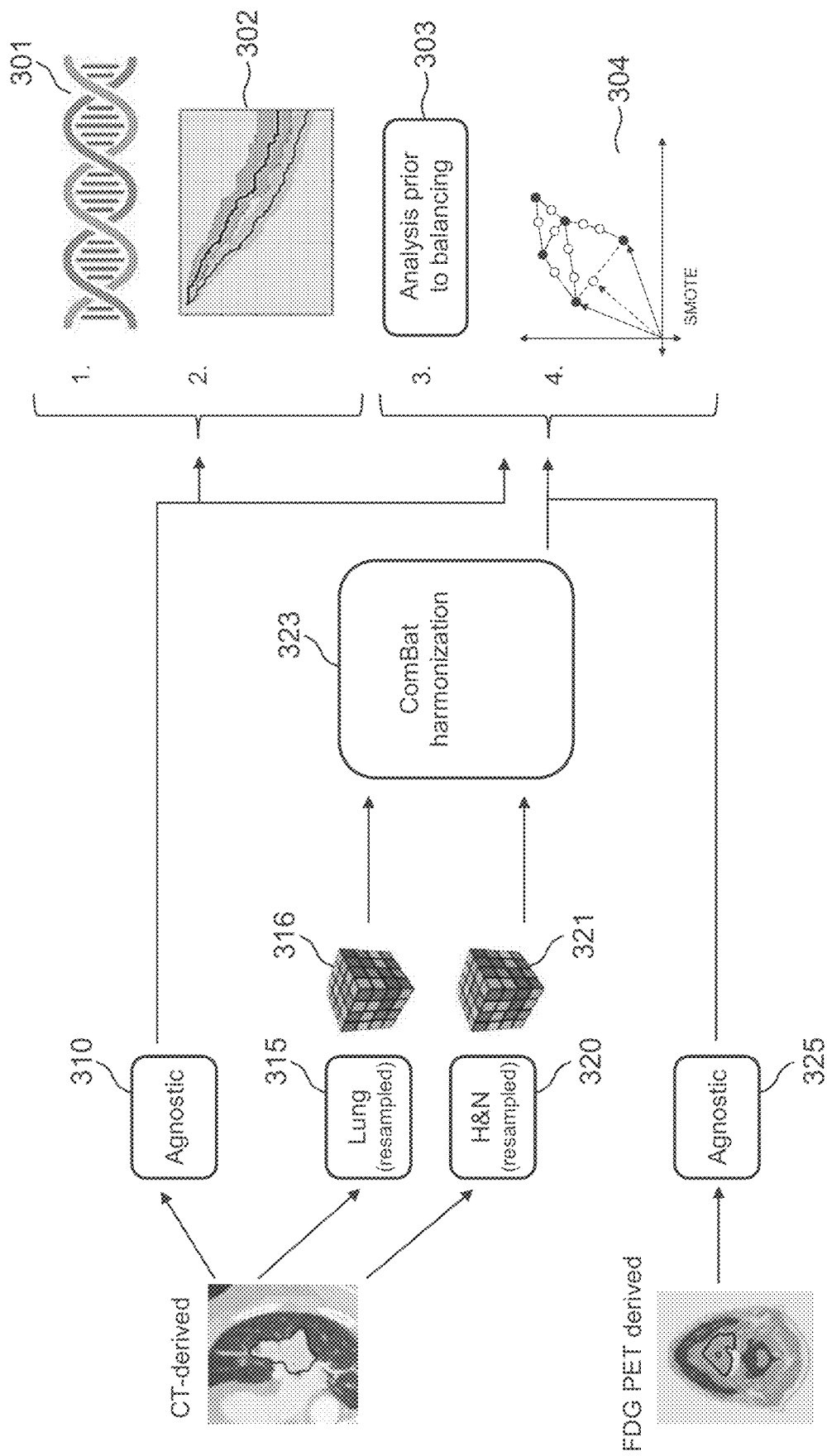
FIG. 3 illustrates certain pre-processing steps to harmonize data, prior to carrying out a method in accordance with the present invention.

Images from the site-specific models were resampled to a voxel size of 1×1×5 mm$^3$ using cubic interpolation (See FIG. 3.). This 'standard' voxel size was chosen according to the highest slice thickness and the median pixel spacing.

Radiomic feature values are potentially sensitive to inter-scanner model, acquisition protocol and reconstruction settings variation. The ComBat statistical feature harmonization technique (Appendix F) was employed in our analysis of features derived from CT. This technique was initially developed by Johnson et al. for gene expression microarray data (even for small sample sizes) and was recently exploited in multicenter PET, MRI and CT radiomic studies.

Machine Learning Model Development and Statistical Analysis

The statistical analysis for model development was performed with R studio software, version 3.3.4 (http://www.R-project.org). The R packages used in this study are described in Appendix G.

The independent samples Mann-Whitney test was used for comparison of unpaired, continuous data and the chi-square and Fisher's exact test was used for the comparison of categorical variables. All reported statistical significance levels were two-sided, with a significance level <0.05.

A random forest (RF) machine-learning classifier was computed (default settings: 500 trees, mtry=√nr. of predictors), with a 10-fold cross validation treebag recursive feature elimination algorithm (Caret package) loop reshuffled 10 times (outer resampling method whereby features were re-ranked) was used to classify patients as hypoxia-positive/negative based on the optimal combination of radiomic features (final RF model based on nr. of features corresponding to first peak in accuracy in the out of bag training cases). Regression trees were generated in order to treat the hypoxic fractions as a continuous variable.

Recursive feature elimination (RFE) is a feature selection method based on iterative model construction (e.g RF) to select features according to their performance (e.g classification error, importance) setting one subset of features aside and then repeating the process with the rest of the features, until all features in the dataset are exhausted. Features are then ranked according to when they were eliminated. As such RFE is a greedy optimization procedure.

For both the CT and FDG-PET model a synthetic minority over-sampling method (SMOTE) was used in R studio ('smotefamily' package, K=5 nearest neighbors used for generating data) on the training dataset in order to achieve balanced classes. SMOTE is an oversampling technique that synthesizes a new minority instance (in feature space) between a minority instance and one of its K nearest neighbors. The order in which the features were (pre-) processed were as following: Resampling→Feature extraction→ComBat→SMOTE→Recursive Feature Elimination→Random Forrest.

In order to ascertain the feasibility of both agnostic (multiple solid tumor subsites such as esophagus, pancreas, lung and head and neck) as well as site-specific (lung and head and neck) hypoxia signatures we have generated the models represented in FIG. 3. Further details on the partitioning of the agnostic CT/FDG-PET models are presented in FIG. 4.

The CT's of 89 mainly early stage lung cancer patients acquired prior to surgery were downloaded from The Cancer Imaging Archive (TCIA).

Primary GTV's were defined for n=80 NSCLC patients, the rest was omitted due to lack of unclear tumor boundaries on CT without availability of [$^{18}$F]-FDG PET.

Radiomic features were extracted from these images and agnostic $CT_{non-SMOTE}$ hypoxia signature outcome classes were generated according to the model coefficients. Corresponding microarray data acquired for the imaging samples were available at National Center for Biotechnology Information (NCBI) Gene Expression Omnibus (GEO: http://www.ncbi.nlm.nih.gov/geo/query/acc.cgi?acc=GSE58661).

Figure 6:
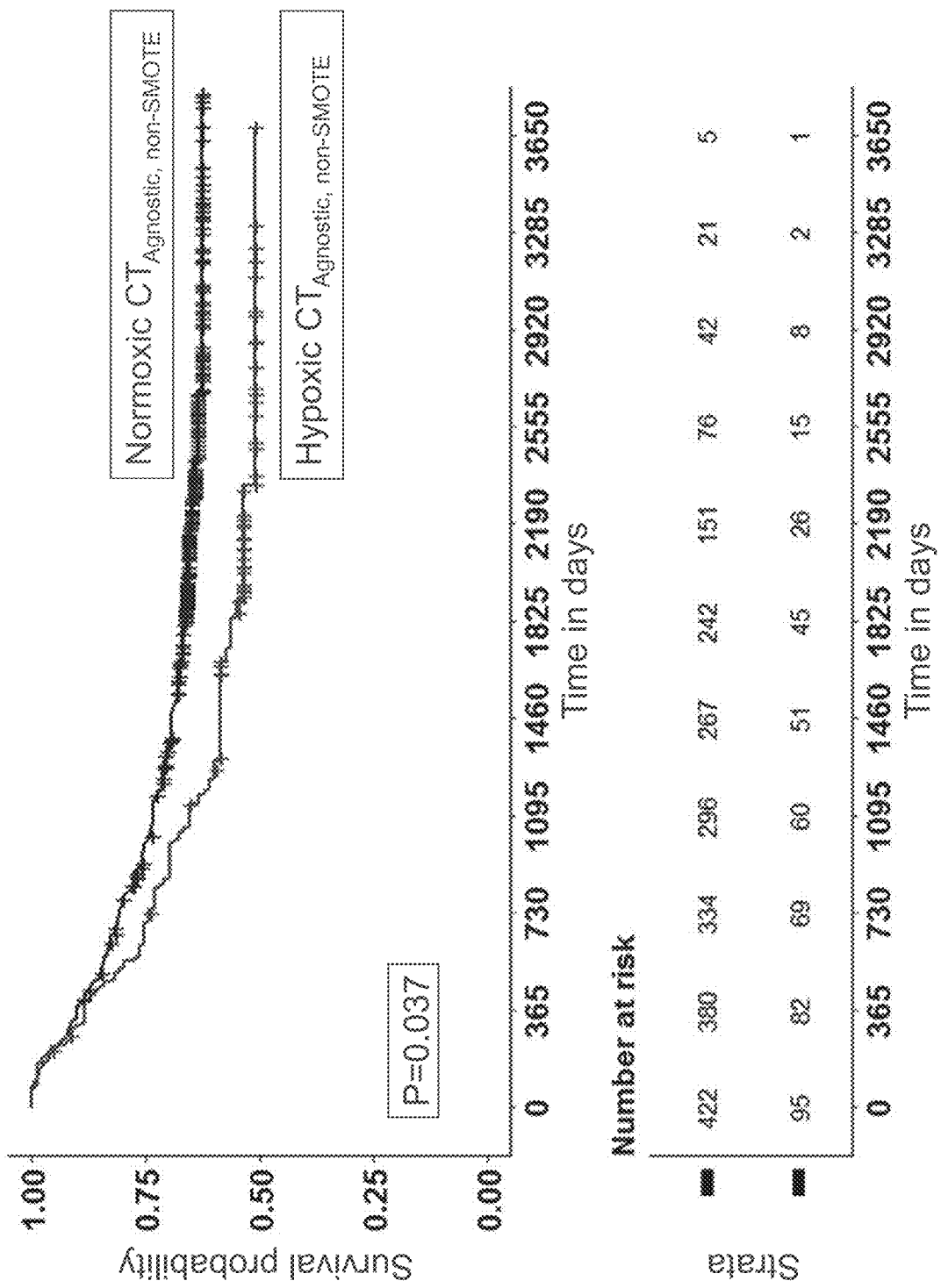
FIG. 6 provides clinical survival data from a head and neck cohort of n=517 oropharyngeal head and neck squamous cell carcinoma patients.

Clinical survival data was collected from yet another external head and neck cohort of n=517 oropharyngeal head and neck squamous cell carcinoma patients from the Princess Margaret Cancer Centre in Toronto (details on this cohort are described in FIG. 6). Radiomic features were subsequently extracted from these images and agnostic $CT_{non-SMOTE}$ hypoxia signature outcome classes were generated according to the model coefficients. Baseline demographic and disease characteristics of these head and neck cohort patients (n=517) are provided in the table below:

| Characteristic | Subgroup | Hypoxic classified (n = 95) | Non-hypoxic classified (n = 422) | P-value |
|---|---|---|---|---|
| Age | Median (range) - yr | 61.9 (39-86.8) | 60.05 (33-89.2) | 0.09 |
|  | <65 yr - no. (%) | 58 (61.1%) | 289 (68.5%) |  |
|  | ≥65 yr - no. (%) | 37 (38.9%) | 133 (31.5%) |  |
| Gender | Male - no. (%) | 76 (80.0%) | 340 (80.6%) | 0.89 |
|  | Female - no. (%) | 19 (20.0%) | 82 (19.4%) |  |
| Pack years | Median (range) - yr | 20 (0-100) | 20 (0-135) | 0.97 |
| ECOG performance status score | Unknown - no. (%) | 1 (1.1%) | 9 (2.1%) | 0.08 |
|  | 0 - no. (%) | 51 (53.7%) | 275 (65.2%) |  |
|  | 1 - no. (%) | 35 (36.8%) | 94 (22.3%) |  |
|  | 2 - no. (%) | 6 (6.3%) | 36 (8.5%) |  |
|  | 3 - no. (%) | 2 (2.1%) | 7 (1.7%) |  |
|  | 4 - no. (%) | 0 (0%) | 1 (0.2%) |  |
| TNM stage | I - no. (%) | 2 | 4 | 0.08 |
|  | II - no. (%) | 2 | 27 |  |
|  | III - no. (%) | 10 | 65 |  |
|  | IVa - no. (%) | 64 | 280 |  |
|  | IVb - no. (%) | 17 | 46 |  |
| HPV status (P16) | Positive - no. (%) | 96 | 27 | 0.51 |
|  | Negative - no. (%) | 246 | 52 |  |
|  | Unknown - no. (%) | 80 | 16 |  |
| Tumor site | Oropharynx - no. (%) | 95 (100%) | 422 (100%) | — |
| Treatment | Radiotherapy alone - no. (%) | 38 | 186 | 0.66 |
|  | Radiotherapy + BGPR inhibitor - no. (%) | 8 | 28 |  |
|  | Concurrent chemoradiation - no. (%) | 49 | 208 |  |

Radiomics Quality Assurance and TRIPOD Statement

For additional quality assurance a radiomics quality score (RQS) was calculated.

Scores were likewise calculated for the 22-item adherence data extraction checklist of the TRIPOD (Transparent reporting of a multivariable prediction model for individual prognosis or diagnosis.

Results

A total of 808 patients with imaging data were included, from which 221 patients with ground-truth hypoxia-PET: 131 patients with [$^{18}$F]-HX4 PET, 14 patients with up to three [$^{18}$F]-FAZA imaging timepoints (n=36) and 76 patients with [$^{18}$F]-FMISO-PET. From this total group 61 patients had available FDG-PET images acquired within a week of hypoxia-PET. One lesion was delineated per patient. In the appendix at the end of the description, with reference to FIGS. 5A to 5D, an elaborate presentation of all model performances and a reflection of underlying class distributions is provided.

The agnostic $CT_{non-SMOTE}$ RF model reached an AUC of 0.77±0.10 in the CT training set (n=100) with a 10-fold cross validation loop reshuffled 10 times, an AUC of 0.75±0.18 in the Boston/NKI validation dataset (n=31), an AUC of 0.73±0.15 on the MSKCC and an AUC of 0.71±0.18 in the UCL validation set (n=36) by combining 12 CT-derived radiomic features to classify hypoxia according to a HF cutoff of 20%. Accuracy in the Boston/NKI validation dataset was 74%, 64% in the MSKCC dataset and 63% in the UCL validation set, with positive and negative predictive values (PPV, NPV) of 70% and 82% for Boston/NKI, 65% and 50% for UCL and 89 and 37% for MSKCC respectively.

An agnostic FDG-PET$_{non}$-SMOTE model reached an AUC of 0.48±0.30 in external validation by combining 5 FDG-PET derived radiomic features to classify hypoxia according to a HF cutoff of 20%. Accuracy in validation was 57% with a PPV of 68.8% and an NPV of 20.0%.

An agnostic FDG-PET$_{SMOTE}$, model reached an AUC of 0.74±0.23 in external validation by combining 10 FDG-PET derived radiomic features to classify hypoxia according to a HF cutoff of 20%. Accuracy in validation was 71% with a PPV of 91.7% and an NPV of 44.4%.

For the lung-specific CT$_{non-SMOTE, ComBat}$ signature the agnostic RF model reached an AUC of 0.75±0.14 in training (n=62, Boston, MASTRO nitro/PET-boost) and an AUC of 0.80±0.15 in the validation set (UCL) by combining 4 CT-derived radiomic features (HF cutoff 20%).

For the H&N-specific CT$_{non-SMOTE, ComBat}$ signature the agnostic RF model reached an AUC of 0.76±0.13 in training (n=76, MSKCC) and an AUC of 0.86±0.20 in the validation set (MAASTRO, NKI) by combining 6 CT-derived radiomic features (HF cutoff 20%).

A total of 72/75 validated hypoxia response-genes identified throughout five literature studies (See Appendix E) were extracted from the NCBI cohort. The agnostic CT$_{non-SMOTE}$ hypoxia signature on the TCIA Lung3 dataset resulted in a total of n=74 NSCLC patients being classified as non-hypoxic and n=6 as hypoxic (7.5%). The Spearman correlation coefficients between gene and radiomic features were relatively low, ranging between −0.49 and 0.43 (See Appendix E for correlation heatmaps). After correction for multiple testing (Benjamini-Hochberg) a total of 117 gene-radiomic features were significantly associated with each other.

According to the agnostic CT$_{non-SMOTE}$ signature a total of n=422 HNSCC patients from the external PMH dataset were classified as non-hypoxic and n=95 HNSCC as hypoxic (18.4%).

Kaplan-Meier analysis (See FIG. 6.) revealed a significant (P=0.037) split in overall survival (OS) between the hypoxic/normoxic classified strata (HR: 1.4 CI: 1.0-2.0). Other between-group patient characteristics are presented in Table 1. Results according to the HPV-status were further elaborated in Appendix D.

For initial quality assurance of the radiomics workflow the outcomes of the entire CT cohort was randomized. Training a CT$_{non-SMOTE}$-model on the randomized outcomes resulted in an AUC of 0.59±0.19 in external validation. The radiomics quality score (RQS) was calculated. This resulting in a score of 67% (most points allocated prospective trial inclusion, 3 external validation datasets and use of feature reduction analysis). Scores were likewise calculated for the 22-item adherence data extraction checklist of the TRIPOD (Transparent reporting of a multivariable prediction model for individual prognosis or diagnosis), which was in the ranged of 0.86-0.92 statement (See Supplementary Appendix H).

Discussion

This study explores the possibility of obtaining a validated radiomics signature consisting of CT and FDG-PET derived imaging features for the prediction of tumor oxygenation status from routine medical images. When applied to the external validation datasets, our models yielded an AUC of 0.79±0.16 (Boston-NKI) and 0.76±0.18 (UCL) for CT, 0.74±0.13 for FDG-PET, and 0.88±0.17 for the combined CT and FDG-PET model. Furthermore Kaplan-Meier analysis revealed a significant (P<0.05) split in terms of overall survival (OS) between the hypoxic and non-hypoxic CT-classified strata in an external HNSCC cohort. There were a total of 117 significant though low correlations between hypoxia response gene-radiomic features from the CT$_{Agnostic, non-SMOTE}$-signature after correction for multiple testing.

The relatively high positive predictive values in nearly all models in our opinion are a strong argument that the signature could be implemented as a usable tool for e.g FLASH, HAP-trial patient selection, which does not directly come out of the AUC's presented (still a lot of false positives and negatives).

To our knowledge this is the first study to train a radiomic signature that is able to predict solid tumor hypoxia derived from HF's inferred from [$^{18}$F]-HX4 imaging instead of a TBR$_{max}$ threshold on one single voxel. Another benefit over previous study was the use of robust feature reduction and advanced machine learning methods on a wide array of solid tumors, the use of separate external datasets, identification of high- and low probability of survival patient groups classified according to the hypoxia signature and the association between hypoxia imaging biomarkers and hypoxia-response genes.

We believe that although the agnostic CT radiomic signature only misclassified 3/40 patients on the ARCON dataset there is still some discrepancy between HX4 spatially derived (volumetric) information and single-section biopsy-derived pimonidazole immunohistochemical staining.

Eventually the choice of cutoff thresholds (primarily HF 20%) was based on previous radiobiologic studies, e.g. Moulder and Rochwell et al, which reviewed 92 HF determinations in 42 tumor systems. Most solid tumors, even those with diameters of 1-3 mm, exhibit according to this study HF's that may range from 10 to 30%. In most experimental solid tumors, ~10-20% of the viable tumor cells are found to be sufficiently hypoxic to be fully radioresistant as measured by analyses of tumor cell survival, tumor growth, or tumor cure.

Wavelet transform is used in image processing to quantify textures in the frequency space at a certain time point, which is useful for image compression and de-noising. The features derived in e.g. the CT$_{SMOTE}$ model were mainly texture and statistical-related (after wavelet decomposition in different sub-bands, so different sharpening and smoothing filters had to be applied initially): in total three texture and two statistical features in the model.

The finding of highly ranked wavelet features could be attributed to the fact that non enhanced CT images were used in the training and validation of the model, possibly introducing discrepancies in Poisson noise and image resolution. An interesting finding is that of the multiple high total lesion glycolysis features (SUV$_{mean}$ X metabolic tumor volume) found in both FDG-PET and combined CT and FDG-PET models. We hypothesize that oxygen availability to cells decreases glucose oxidation, whereas oxygen shortage in hypoxic solid tumors consumes glucose faster in an attempt to produce ATP via the less efficient anaerobic glycolysis to lactate (Pasteur effect).

Hypoxia-PET has been previously shown to provide reproducible and spatially stable results, significant spatial correlations with metabolic active tumor volumes on FDG-PET and prognostic value with regard to disease free survival and local tumor control. Hence we believe we have identified a good ground truth measurement of hypoxia status for comparison to CT/FDG-PET derived radiomics in the context of patient stratification for hypoxia-activated prodrug trials albeit with radiotherapy (e.g dose-escalation, dose-painting of hypoxic subvolumes) or systemic therapy (e.g hypoxic cytotoxic agents, immunotherapy). Other strengths of this study are the use of a robust feature selection and machine learning classifier in order to train and validate the eventual models. Further strengths are the validation on multiple external cohorts and the assessment of hypoxia according to HF's.

Some limitations include: (i) The unbalanced data, which we have tried to account for by applying SMOTE analysis. (ii) In this cross-sectional study there is the concern that solid tumors are riddled with areas of mild-hypoxia leading to severe hypoxia and necrosis as well areas of acute hypoxia and re-oxygenation. The chaotic architecture of the tumor vasculature typically results in dynamic fluctuations in blood flow and therefore oxygen availability. These fluctuations result in distinctive patterns and represent a phenomenon described as 'cycling hypoxia', with frequencies that have been shown to vary between seconds to hours and even days. (iii) No test-retest analysis was performed to rank features according to their temporal reproducibility/ stability. (iv) Despite the fact that our main CT models are trained and validated using HX4-PET with similar acquisition times, the addition of other tracers and times decreases the accuracy and robustness of the study.

With prospect to the future, the accurate quantification of hypoxia using PET requires modelling of—and correcting for—tracer properties, notably, the tracer distribution volume $V_d$. Currently, such modelling requires a long dynamic PET imaging protocol, which places a greater burden on patients and machine workload, further impeding the uptake of hypoxia-PET imaging into clinical practice. Hence, there is a pressing need to develop simplified cost-efficient imaging biomarkers that correct for inter-patient PET imaging agent transport variances.

Future research should in our view focus on the accrual of larger amounts of patients in disease-specific hypoxia-PET trials, further improving acquisition timing and signal stability in hypoxia PET scanning protocols, correlating hypoxia PET-radiomics with 3D tumor histology, associating robust gene expression signatures with hypoxia radiomic signatures and training and validating models on higher volumes of data using the distributed learning approach.

In summary, our results indicate that a CT and [$^{18}$F] FDG-PET derived radiomic signature can both accurately classify tumor hypoxia according to literature-derived HF cutoffs. These findings further reinforce the assumption that we can "enrich" future interventional trials with hypoxia-targeting agents and FLASH by identifying patients with tumors likely to be hypoxic. After validation on multi-institutional cohorts such a marker could be potentially useful for patient stratification in trials and situations where [$^{18}$F]-HX4 is not readily available.

The present invention has been described in terms of some specific embodiments thereof. It will be appreciated that the embodiments shown in the drawings and described herein are intended for illustrated purposes only and are not by any manner or means intended to be restrictive on the invention. It is believed that the operation and construction of the present invention will be apparent from the foregoing description and drawings appended thereto. It will be clear to the skilled person that the invention is not limited to any embodiment herein described and that modifications are possible which should be considered within the scope of the appended claims. Also kinematic inversions are considered inherently disclosed and to be within the scope of the invention. Moreover, any of the components and elements of the various embodiments disclosed may be combined or may be incorporated in other embodiments where considered necessary, desired or preferred, without departing from the scope of the invention as defined in the claims.

In the claims, any reference signs shall not be construed as limiting the claim. The term 'comprising' and 'including' when used in this description or the appended claims should not be construed in an exclusive or exhaustive sense but rather in an inclusive sense. Thus the expression 'comprising' as used herein does not exclude the presence of other elements or steps in addition to those listed in any claim. Furthermore, the words 'a' and 'an' shall not be construed as limited to 'only one', but instead are used to mean 'at least one', and do not exclude a plurality. Features that are not specifically or explicitly described or claimed may be additionally included in the structure of the invention within its scope. Expressions such as: "means for . . . " should be read as: "component configured for . . . " or "member constructed to . . . " and should be construed to include equivalents for the structures disclosed. The use of expressions like: "critical", "preferred", "especially preferred" etc. is not intended to limit the invention. Additions, deletions, and modifications within the purview of the skilled person may generally be made without departing from the spirit and scope of the invention, as is determined by the claims. The invention may be practiced otherwise then as specifically described herein, and is only limited by the appended claims.

Figure Legend

FIG. 1. Workflow resulting in [$^{18}$F]-HX4 and [$^{18}$F]-FDG-PET radiomic feature extraction and calculation of HF's on [$^{18}$F]-HX4. GTV delineations on diagnostic/baseline planning CT were rigidly registered onto the HX4-CT and contour transformation was performed from pre-treatment diagnostic/planning CT onto fused HX4 PET/CT.

FIG. 2A. Transversal 3D view of fused [$^{18}$F]-HX4 PET/ CT with primary non-small cell lung tumor (NCT01024829 trial) in right lower lobe (white: non-hypoxic, red: hypoxic region).

FIG. 2B. Transversal 2D multislice view of hypoxic classified non-small cell lung carcinoma (NSCLC) patient (NCT01024829 trial) with defined primary gross tumor volume contour on CT (green). Note that through the prism of a radiologist, based on a non-perfusion lung CT alone no signs (e.g regions of decreased attenuation, necrotic core) point to the fact that this tumor is hypoxic.

FIG. 2C. Transversal 2D multislice view of hypoxic H&N squamous cell carcinoma (HNSCC) patient (NCT01504815 trial) with defined primary gross tumor volume (green) contour on fused [$^{18}$F]-HX4 PET/CT. High HX4 uptake areas can be seen within the primary gross tumor region.

FIG. 3. Workflow of generated hypoxia-classification models. The agnostic classification signature was used to assess the association with the most relevant literature-derived hypoxia-response genes (1) and the prognostic value on an independent validation cohort (2). All generated signature performances were assessed prior to and after SMOTE (3-4).

Site-specific (H&N, Lung) CT images were resampled to 1×1×5 mm$^3$ and radiomic feature values were harmonized, while agnostic features were directly analyzed before and after balancing the outcome classes.

Figure 4A:
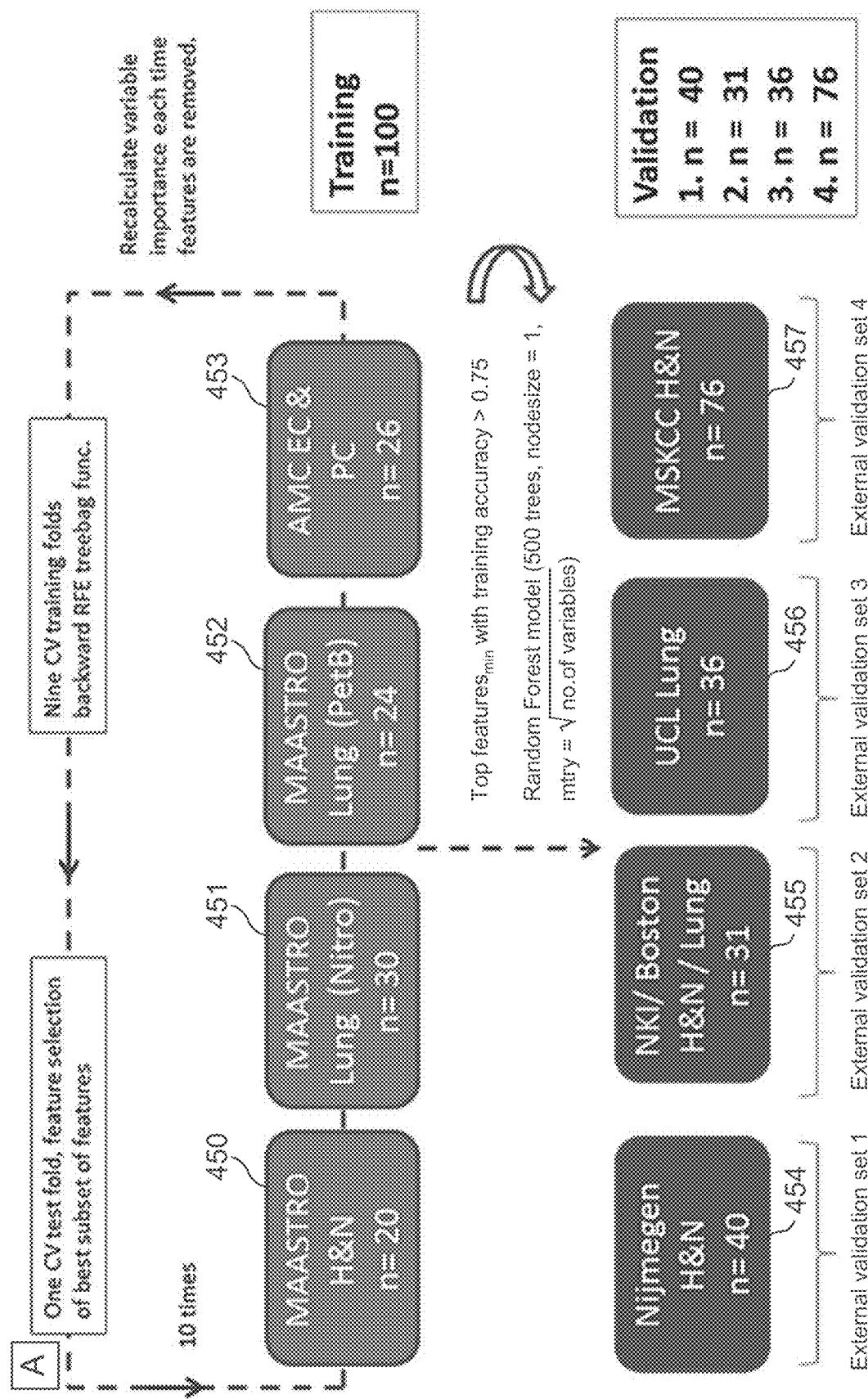
FIGS. 4A and 4B illustrate details on the partitioning of agnostic CT/ FDG-PET models to be used in a method in accordance with the present invention.

FIG. 4A. Flow chart of procedural steps to derive predictive agnostic CT model, including (1) feature selection (recursive feature elimination), (2) model training, and (3) External validation.

Figure 4B:
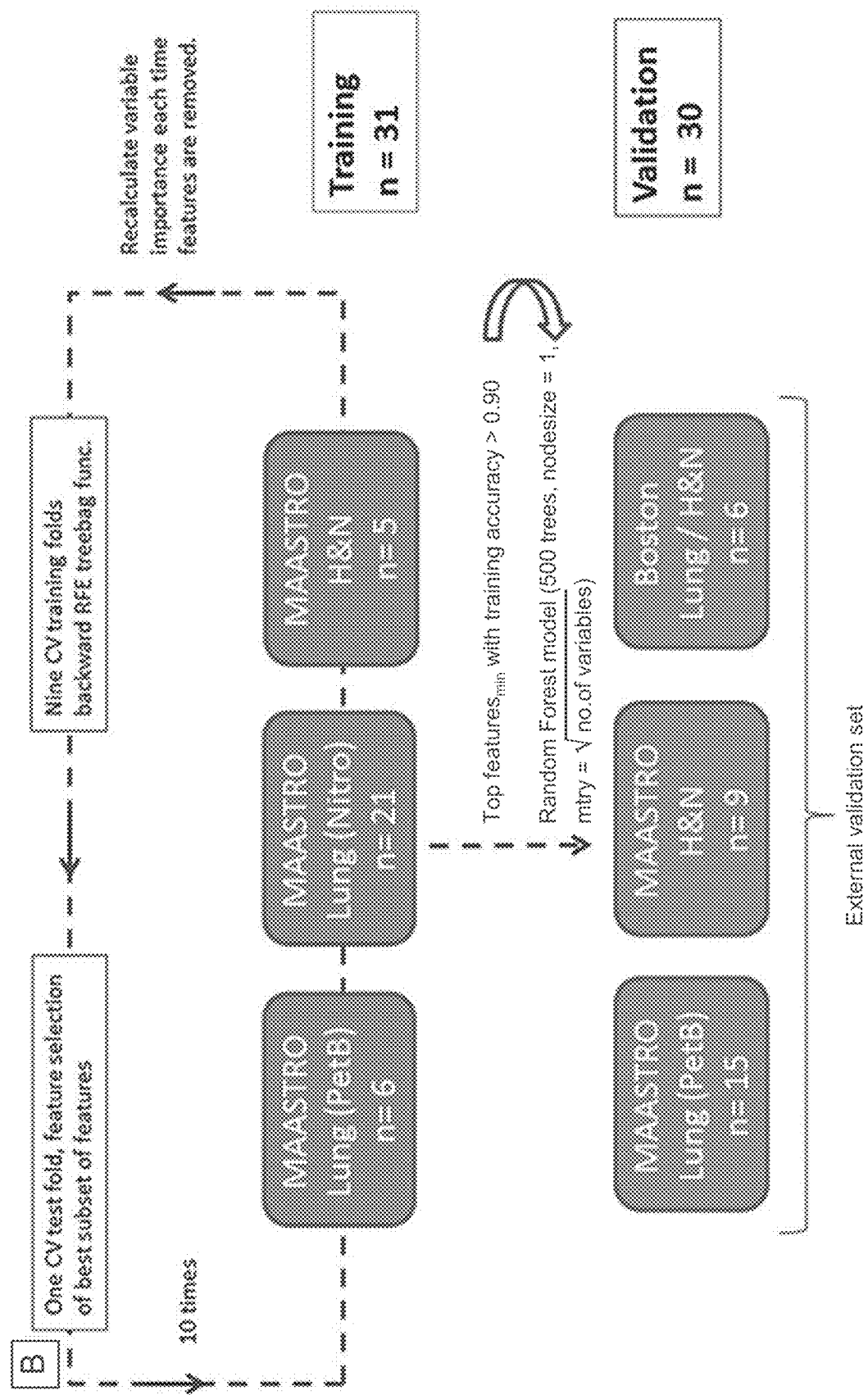

FIG. 4B. Flow chart of procedural steps to derive predictive agnostic FDG-PET model.

Figure 5A:
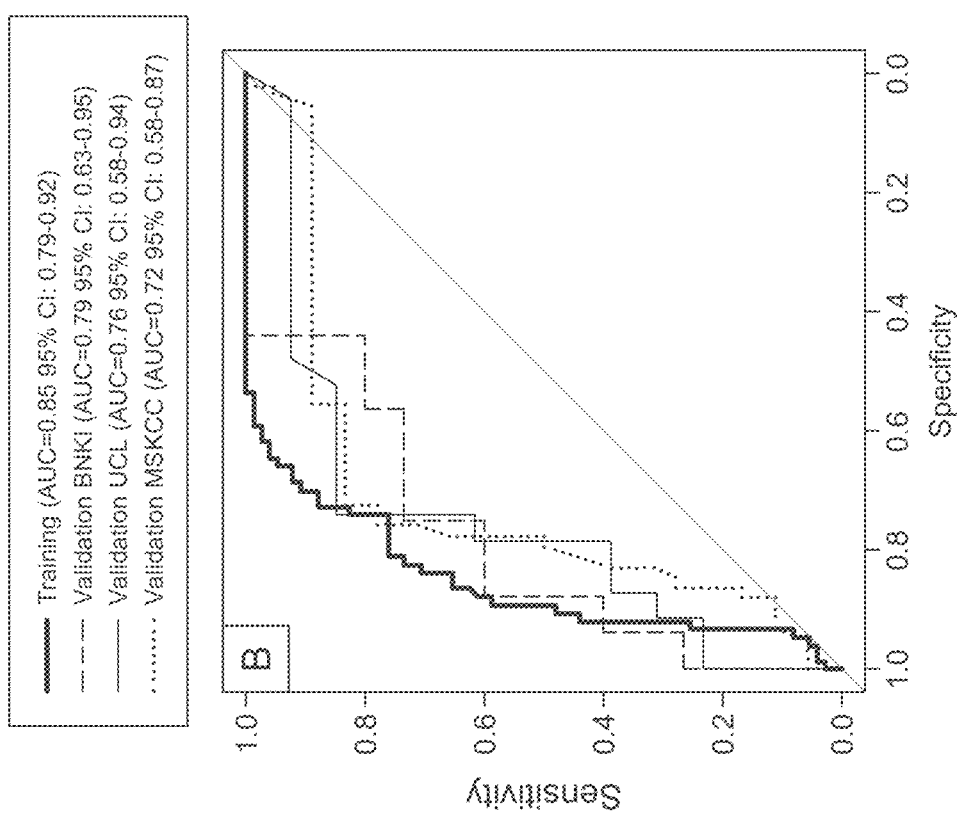
FIGS. 5A, 5B, 5C, and 5D provide a presentation of model performances and a reflection of underlying class distributions.

FIG. 5A. Training and validation AUC's presented for HF cutoff of 20% in agnostic CT model.

Figure 5B:
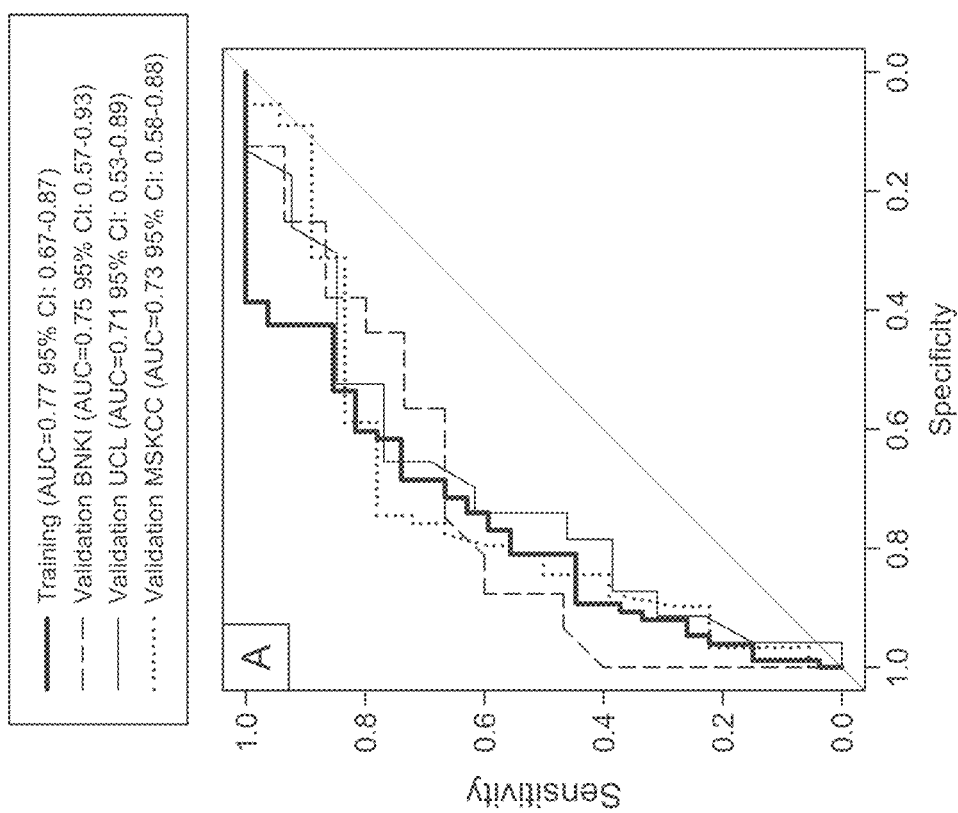

FIG. 5B. Training and validation AUC presented for HF 20% cutoff in agnostic $CT_{SMOTE}$ model.

Figure 5C:
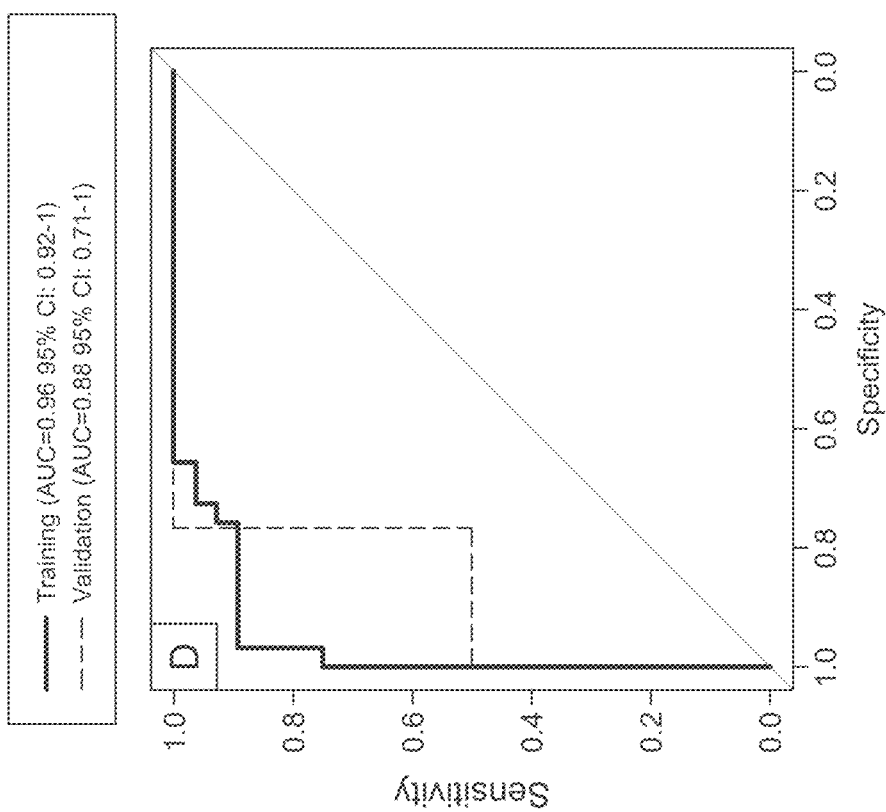

FIG. 5C. Training and validation AUC presented for HF 20% cutoff in agnostic $FDG-PET_{SMOTE}$ model.

Figure 5D:
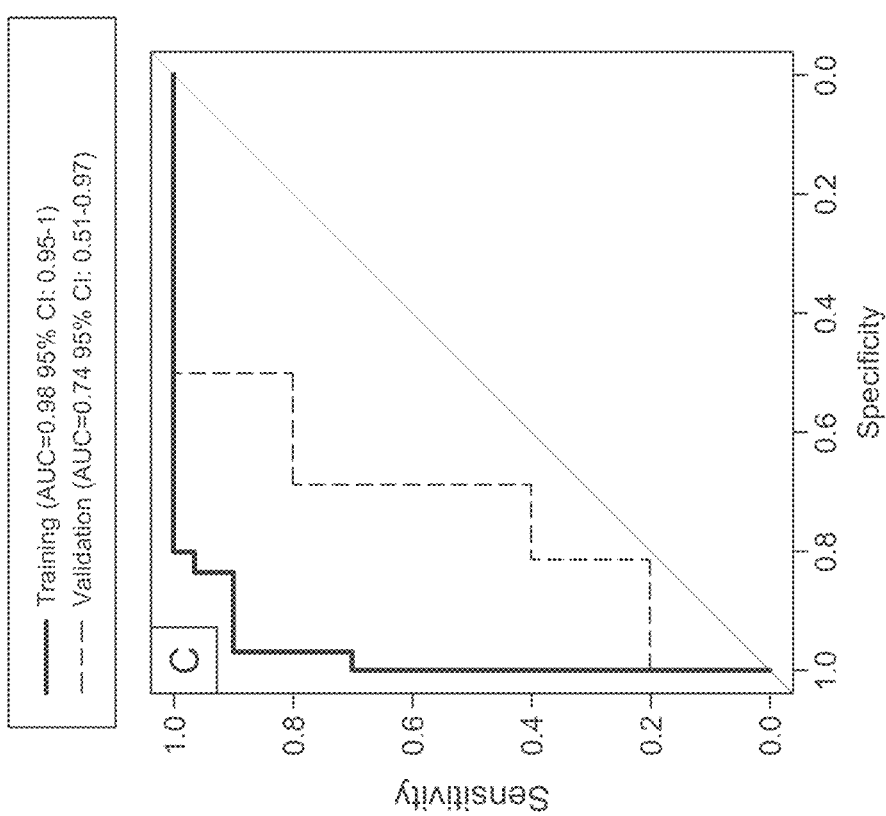

FIG. 5D. Training and validation AUC presented for HF 20% cutoff in agnostic ($CT+FDG-PET_{SMOTE}$ model. e. Summary of agnostic and site-specific model performance parameters according to HF 20% threshold. Validation datasets were constructed and numbered as following: (1) BostonNKI (2) UCL (3) MSKCC.

FIG. 6. Kaplan-Meier survival curves for overall survival (OS) according to the $CT_{Agnostic, non-SMOTE}$ hypoxia signature predicted classes on PMH head and neck cohort (n=517).

APPENDIX

Agnostic and Site-specific Model Features, Confusion Matrix and Calibration Plots for 20% Hypoxic Fraction Cutoff Agnostic CT-derived Radiomic Hypoxia Classifier A subset of patients in 3 MAASTRO and 1 AMC datasets were used for training the agnostic CT-radiomics model, while the remaining MSKCC, Radboud UMC (ARCON), Boston, NKI and UCL datasets were held out for separate external validation. The reasoning behind this partitioning choice and the heterogeneous group of solid tumors for the agnostic models was (1) Modern machine learning algorithms require as a rule of thumb 10 patients for each feature in a model based on binary classifiers [29]. Up to 100 training patients were therefore required, depending on the type of model generated. This left us with little choice, other than keeping the MAASTRO datasets together for training together with the AMC cohort, in order to leave sufficient head and neck and lung cases for validation (Boston-NKI cohort). For the FDG-PET model we were left with an even smaller sample size, hence we randomly split the cohort into one training and one validation dataset. (2) We hypothesized that the generalizability of the signature increases as it is trained on a more heterogeneous population. (3) We were curious to discover whether our [$^{18}$F]-HX4-derived signature not only would validate on an external [$^{18}$F]-HX4-cohort, but also on an external pimonidazole staining and [$^{18}$F]-FAZA-cohort.

The agnostic RF model (without SMOTE) reached an AUC of 0.77±0.10 in the CT training set (n=100) with a 10-fold cross validation loop reshuffled 10 times, an AUC of 0.75±0.18 in the Boston/NKI validation dataset (n=31), an AUC of 0.73±0.15 on the MSKCC and an AUC of 0.71±0.18 in the UCL validation set (n=36) by combining 12 CT-derived radiomic features to classify hypoxia according to a hypoxic fraction cutoff of 20%. Accuracy in the Boston/NKI validation dataset was 74%, 64% in the MSKCC dataset and 63% in the UCL validation set, with positive and negative predictive values of 70% and 82% for Boston/NKI, 65% and 50% for UCL and 89 and 37% for MSKCC respectively.

After synthetic minority class oversampling a CT model reached an AUC of in the training set (n=148, hypoxic class n=75 and non-hypoxic class n=73) with 10-fold cross validation loop reshuffled 10 times, an AUC of 0.79±0.16 in the Boston/NKI and 0.76±0.18 in the UCL validation set respectively by combining 5 CT-derived radiomic features to classify hypoxia according to a hypoxic fraction cutoff of 20% (See FIG. 4).

Accuracy in the UCL validation dataset (n=36) was 69% and 61% for the Boston/NKI validation dataset (n=31) with the $CT_{SMOTE}$ model, with positive and negative predictive values of 75%, 58.3% and 70%, 57.1% respectively.

Site-specific CT-derived Radiomic Hypoxia Classifier

For the lung-specific CT signature the agnostic RF model (without SMOTE, with ComBat) (n=62 patients in training; Boston MAASTRO Nitro and MAASTRO PET BOOST) reached an AUC of 0.75±0.14 in training and an AUC of 0.80±0.15 in the validation set (UCL) by combining 4 CT-derived radiomic features to classify hypoxia according to a hypoxic fraction cutoff of 20%.

For the lung-specific CT signature the agnostic RF model (with SMOTE, with ComBat) (n=98 patients in training: Boston MAASTRO Nitro and MAASTRO PET BOOST) reached an AUC of 0.89±0.07 in training and an AUC of 0.76±0.17 in the validation set (UCL) by combining 3 CT-derived radiomic features to classify hypoxia according to a hypoxic fraction cutoff of 20%.

For the head and neck-specific CT signature the agnostic RF model (without SMOTE, with ComBat) (n=76 patients in training) reached an AUC of 0.76±0.13 in training (MSKCC) and an AUC of 0.86±0.20 in the validation set (MAASTRO, NKI) by combining 6 CT-derived radiomic features to classify hypoxia according to a hypoxic fraction cutoff of 20%.

For the head and neck-specific CT signature the agnostic RF model (with SMOTE, with ComBat) (n=118 patients in training) reached an AUC of 0.96±0.04 in training (MSKCC) and an AUC of 0.84±0.20 in the validation set (MAASTRO, NKI) by combining 15 CT-derived radiomic features to classify hypoxia according to a hypoxic fraction cutoff of 20%.

Additional Validation (Different Thresholds, ARCON Biopsy) for Hypoxia Classification on CT In the external pimonidazole ARCON dataset (ARCON) [20] only 3/40 patients were misclassified as hypoxic (false positive) according to the $CT_{Agnostic, non-SMOTE}$ signature, while 0/40 patients had a positive staining fraction >20% and were correctly classified as non-hypoxic (no false negatives). The AUC values with $CT_{SMOTE}$ in the Boston-NKI dataset were 0.64±0.12 and 0.63±0.22 for the 10% and 30% hypoxic threshold respectively. For the UCL dataset the AUC values with the $CT_{SMOTE}$ model were 0.71±0.17 and 0.72±0.17 for the 10% and 30% hypoxic threshold respectively.

TABLE 2

Summary of agnostic and site specific model performance parameters according to HF20% threshold.
Validation datasets were constructed and numbered as following: (1) BostonNKI (2) UCL (3) MSKCC:

| Model | Patients training | Number features in model | AUC external validation | Confidence Interval | Accuracy testing | Confidence Interval | PPV (%) | NPV (%) |
|---|---|---|---|---|---|---|---|---|
| $CT_{Agnostic}$ | 100 | 12 | 1. 0.75 | 1. [0.57, 0.93] | 1. 0.74 | 1. [0.55, 0.58] | 1.70 | 1.81 |
| | | | 2. 0.71 | 2. [0.53, 0.89] | 2. 0.64 | 2. [0.46, 0.79] | 2.65 | 2.50 |
| | | | 3. 0.33 | 3. [0.58, 0.89] | 3. 0.63 | 3. [0.51, 0.74] | 3.89 | 3.37 |
| $FDG_{Agnostic}$ | 40 | 5 | 0.48 | [0.18, 0.79] | 0.57 | [0.34, 0.78] | 68.8 | 20.0 |
| $CT_{Agnostic, SMOTE}$ | 148 | 5 | 1. 0.79 | 1. [0.63, 0.95] | 1. 0.61 | 1. [0.42, 0.78] | 1.70 | 1.57 |
| | | | 2. 0.76 | 2. [0.58, 0.94] | 2. 0.69 | 2. [0.52, 0.84] | 2.75 | 2.58 |
| | | | 3. 0.72 | 3. [0.58, 0.87] | 3. 0.51 | 3. [0.40, 0.63] | 3.92 | 3.31 |
| $FDG_{Agnostic, SMOTE}$ | 60 | 10 | 0.74 | [0.51, 0.97] | 0.71 | [0.48, 0.99] | 91.7 | 44.4 |
| $(CT + FDG)_{Agnostic, SMOTE}$ | 57 | 15 | 0.88 | [0.71, 1.0] | 0.76 | [0.52, 0.92] | 92.9 | 42.9 |
| $CT_{Lung, ComBat}$ | 62 | 4 | 0.80 | [0.65, 0.94] | 0.64 | [0.46, 0.879] | 100 | 50 |
| $CT_{Lung, SMOTE, ComBat}$ | 98 | 3 | 0.76 | [0.59, 0.92] | 0.72 | [0.54, 0.86] | 81 | 60 |
| $CT_{H\&N, ComBat}$ | 76 | 6 | 0.86 | [0.66, 1.00] | 0.86 | [0.68, 0.96] | 83 | 100 |
| $CT_{H\&N, SMOTE, ComBat}$ | 118 | 15 | 0.84 | [0.64, 1.00] | 0.76 | [0.56, 0.90] | 88 | 58 |

The invention claimed is:

1. A method of training a machine learning data processing model for determining a hypoxia status of a neoplasm in a human or animal body, wherein the machine learning data processing model is a random forest data processing model, the method comprising:
   obtaining, for each of a plurality of neoplasms, at least one data sample comprising three dimensional imaging data of said respective neoplasm;
   determining, for each data sample, a hypoxic fraction of the neoplasm by identifying a volume fraction of a total volume of the neoplasm which is indicative of hypoxia, and associating the determined hypoxic fraction with the respective data sample;
   determining, for each data sample, a set of image features comprising a plurality of image features associated with the neoplasm, and wherein each image feature of the set of image features is characterized by an image feature parameter value that is derived from the image data;
   iterating a sequence of training steps, wherein the sequence in each iteration includes:
      selecting, for the respective iteration, a subset of image features from the set of image features, wherein at least a part of the selected image features for the subset has not been selected during a preceding iteration;
      eliminating, for each data sample, the subset of image features from the set of image features to yield a reduced set of image features;
      generating, based on the reduced sets of image features for the plurality of data samples and the hypoxic fractions associated with the data samples, a plurality of decision trees and providing a momentary random forest model based on the decision trees;
      submitting, for at least one test data sample, a test set of image features to the momentary random forest model to determine the hypoxia status for the at least one test data sample, and compare the determined hypoxia status with the hypoxia fraction associated with the test data sample to yield a performance value;
   continuing the step of iterating until each of the image features has been selected for a subset at least once;
   selecting, by evaluating the performance values, a plurality of preferred image features from the set of image features for providing a radiomics feature signature including the preferred image features; and
   providing the trained random forest data processing model based on decision trees associated with the preferred image features of the radiomics feature signature.

2. The method according to claim 1, wherein the momentary random forest models and the trained random forest data processing model are at least one of:
   classifier models, wherein the hypoxia status provides a Boolean indication on whether or not a data sample is indicative of a hypoxic neoplasm; or
   regression models, wherein the hypoxia status provides an expectation value of a hypoxic fraction of the neoplasm associated with the data sample.

3. The method according to claim 1, wherein the imaging data is obtained after administration of a hypoxiaPET tracer, and wherein, for determining the hypoxia fraction, the volume fraction of the total volume of the neoplasm is identified wherein a standard uptake value of the hypoxia staining marker is above a threshold value.

4. The method according to claim 3, wherein determining the hypoxia fraction comprises the steps of:
   determining an average standard uptake value of the hypoxia staining marker in at least a region of the neoplasm;
   determining, for each voxel of a plurality of voxels within the region, a standard uptake value of the respective voxel;
      flagging the respective voxel as a hypoxic voxel if the standard uptake value of the voxel is greater than or equal to 1.4 times the average standard uptake value of the region; and
      flagging the respective voxel as a non-hypoxic voxel if the standard uptake value of the voxel is smaller than 1.4 times the average standard uptake value of the region;
   counting a total number of voxels and a total number of hypoxic voxels, and calculating the hypoxic fraction by dividing the total number of hypoxic voxels by the total number of voxels.

5. The method according to claim 1, wherein after obtaining the data samples, one or more of the data samples are selected as test data samples forming a test fraction and wherein the other data samples of the plurality of data samples provide a training fraction, wherein at least a part of the selected test data samples has not been selected as test data samples during a preceding pass of the method;

wherein the step of generating decision trees for providing the momentary random forest model is performed based on the training fraction and wherein submitting the test set of image features to the momentary random forest model is performed based on the test fraction;

wherein the method is repeated in a plurality of passes.

6. The method according to claim 5, wherein the method is repeated until all data samples of the plurality of data samples have been selected as test data samples at least once.

7. The method according to claim 1, wherein the step of generating the plurality of decision trees comprises generating each decision tree as a sequence of decisions wherein each decision is based on one or more image features of the reduced set, and wherein for selecting the preferred image features the image features are ranked based on the performance values and one or more image features having lowest performance values are discarded.

8. The method according to claim 7 wherein for selecting the preferred image features, during each pass one or more image features having lowest performance values are discarded, such as to yield the preferred image features at the end of the last pass of the method.

9. The method according to claim 1, wherein after having determined the hypoxic fractions of each of the plurality of data samples, a total number of data samples having an associated hypoxic fraction indicative of a hypoxic neoplasm is compared with a total number of data samples having an associated hypoxic fraction indicative of a non-hypoxic neoplasm, and wherein one or more data samples are repeated or discarded if a difference between the total number of hypoxic neoplasms and the total number of non-hypoxic neoplasm exceeds a threshold, such as to balance the data samples used for training the random forest data processing model.

10. The method according to claim 9, wherein the threshold is a difference exceeding 20%.

11. The method according to claim 1, wherein a neoplasm associated with a data sample is flagged as a hypoxic neoplasm if the hypoxic fraction is above at least 5%.

12. The method according to claim 1, wherein the data samples have been obtained using a plurality of different imaging systems, and wherein the method further comprises a step of harmonizing the image features such that the characteristic image feature parameter values are quantitatively comparable.

13. The method according to claim 1, wherein the step of obtaining data samples is performed by selecting data samples of a plurality of neoplasms of a specific phenotype.

14. The method according to claim 13, wherein the neoplasms of the specific phenotype include at least one of a group comprising: head and neck type tumors, lung tumors.

15. A method of determining a hypoxia status of a neoplasm in a human or animal body, wherein the method comprises:

obtaining using an imaging system three dimensional imaging data of said the neoplasm for providing a data sample;

determining a plurality of image features from the data sample wherein each image feature is characterized by an image feature parameter value that is derived from the image data;

submitting the plurality of image features to a trained random forest data processing method;

wherein the trained random forest data processing model is trained using a method according to any one or more of the preceding claims, and wherein the plurality of image features at least include the preferred image features of the radiomics feature signature.

16. A system for determining a hypoxia status of a neoplasm in a human or animal body, wherein the system comprises a memory, a controller and an input wherein the input is configured for receiving a data sample comprising three dimensional imaging data of a neoplasm, wherein the memory has stored therein data descriptive of a trained random forest data processing model that has been trained using a method according to claim 1.

17. The method of claim 9, wherein the threshold is a difference exceeding 10%.

18. The method of claim 9, wherein the threshold is a difference exceeding 5%.

19. The method according to claim 11, wherein a neoplasm associated with a data sample is flagged as a hypoxic neoplasm if the hypoxic fraction is above at least 10%.

20. The method according to claim 19, wherein a neoplasm associated with a data sample is flagged as a hypoxic neoplasm if the hypoxic fraction is above at least 20%.

* * * * *